(12) United States Patent
Jordan et al.

(10) Patent No.: US 9,466,203 B2
(45) Date of Patent: Oct. 11, 2016

(54) SNEAK WATER DETECTION FOR CONCRETE DELIVERY VEHICLES

(71) Applicant: Verifi LLC, West Chester, OH (US)

(72) Inventors: Richard K. Jordan, Littleton, MA (US); Mark F. Roberts, North Andover, MA (US); Eric P. Koehler, Boston, MA (US)

(73) Assignee: GCP Applied Technologies Inc., Cambridge, MA (US)

( * ) Notice: Subject to any disclaimer, the term of this patent is extended or adjusted under 35 U.S.C. 154(b) by 355 days.

(21) Appl. No.: 14/052,289

(22) Filed: Oct. 11, 2013

(65) Prior Publication Data

US 2014/0104066 A1    Apr. 17, 2014

Related U.S. Application Data

(60) Provisional application No. 61/713,914, filed on Oct. 15, 2012.

(51) Int. Cl.

| G08B 21/00 | (2006.01) |
|---|---|
| G08B 21/20 | (2006.01) |
| G01N 33/38 | (2006.01) |
| B28C 5/42 | (2006.01) |
| G01N 11/00 | (2006.01) |

(52) U.S. Cl.
CPC .......... G08B 21/20 (2013.01); B28C 5/422 (2013.01); G01N 33/383 (2013.01); *G01N 2011/0046* (2013.01)

(58) Field of Classification Search
None
See application file for complete search history.

(56) References Cited

U.S. PATENT DOCUMENTS

| 4,008,093 A | 2/1977 | Kitsuda et al. |
|---|---|---|
| 4,318,177 A | 3/1982 | Rapp et al. |
| 4,356,723 A * | 11/1982 | Fay .................. G01N 11/00 73/54.03 |

(Continued)

FOREIGN PATENT DOCUMENTS

| EP | 2165815 | 3/2010 |
|---|---|---|
| GB | 2388055 A | 11/2003 |

(Continued)

OTHER PUBLICATIONS

Thomas, Form PCT/ISA/210, International Search Report for PCT/US2013/064587, dated Feb. 27, 2014, 2 pages.

(Continued)

*Primary Examiner* — Firmin Backer
*Assistant Examiner* — Nay Tun
(74) *Attorney, Agent, or Firm* — Craig K. Leon (57) ABSTRACT

The invention provides a method and system for detecting "sneak" additions of water or other fluid into the mixing drum of a concrete delivery vehicle having an automated rheology (e.g., slump) monitoring system. Sneak fluid additions are detected based on continuous rheology monitoring, even where valves and flow meters on the delivery vehicle are not used for the fluid addition. The invention is effective for monitoring additions by truck drivers who might add water from an undocumented water source (e.g., hose) along the delivery route or at the site, to hasten pouring, placement, and finishing at the time of delivery. Once sneak fluid addition is detected, the methods and system provide for reporting in the form of alerts, alarms, or other indications that sneak fluid addition has occurred, including monitor graphs or printouts confirming existence and/or extent of sneak fluid added into the vehicle mixing drum.

19 Claims, 3 Drawing Sheets

(56) References Cited

U.S. PATENT DOCUMENTS

| | | | |
|---|---|---|---|
| 4,544,275 A | 10/1985 | Hudelmaier | |
| 4,900,154 A | 2/1990 | Waitzinger et al. | |
| 4,964,917 A | 10/1990 | Bobrowski et al. | |
| 5,099,688 A | 3/1992 | De Mars | |
| 5,203,919 A | 4/1993 | Bobrowski et al. | |
| 5,427,617 A | 6/1995 | Bobrowski et al. | |
| 5,713,663 A | 2/1998 | Zandberg et al. | |
| 5,752,768 A * | 5/1998 | Assh | B28C 5/422 366/3 |
| 6,042,258 A | 3/2000 | Hines | |
| 6,042,259 A | 3/2000 | Hines | |
| 6,123,444 A | 9/2000 | Silbernagel | |
| 6,484,079 B2 | 11/2002 | Buckelew et al. | |
| 6,611,755 B1 | 8/2003 | Coffee et al. | |
| 6,892,131 B2 | 5/2005 | Coffee et al. | |
| 7,489,993 B2 | 2/2009 | Coffee et al. | |
| 7,730,903 B2 | 6/2010 | Lindblom et al. | |
| 8,020,431 B2 | 9/2011 | Cooley et al. | |
| 8,118,473 B2 | 2/2012 | Compton et al. | |
| 2002/0015354 A1 | 2/2002 | Buckelew | |
| 2007/0185636 A1* | 8/2007 | Cooley | B28C 5/422 701/50 |
| 2008/0316856 A1* | 12/2008 | Cooley | B28C 5/422 366/142 |
| 2010/0031243 A1 | 2/2010 | Jakubowski | |
| 2011/0004333 A1* | 1/2011 | Andersen | C04B 40/0032 700/103 |
| 2011/0029134 A1 | 2/2011 | Hazrati et al. | |
| 2011/0320040 A1 | 12/2011 | Koehler et al. | |
| 2012/0016523 A1* | 1/2012 | Koehler | G01N 11/00 700/265 |
| 2012/0020180 A1 | 1/2012 | Koehler et al. | |
| 2012/0204625 A1 | 8/2012 | Beaupre et al. | |
| 2012/0250446 A1 | 10/2012 | Cook et al. | |
| 2013/0145967 A1 | 6/2013 | Koehler et al. | |

FOREIGN PATENT DOCUMENTS

| | | | |
|---|---|---|---|
| WO | 2007060272 | 5/2007 | |
| WO | 2009144523 | 3/2009 | |
| WO | 2010111204 | 9/2010 | |
| WO | WO 2010110814 A1 * | 9/2010 | G01N 11/00 |

OTHER PUBLICATIONS

Thomas, Form PCT/ISA/237, Written Opinion of the International Searching Authority for PCT/US2013/064587, dated Feb. 27, 2014, 4 pages.

* cited by examiner

Fig. 1

History of Additions by Truck

7:48 AM

| | |
|---|---|
| Water (gal/yd³) | 0.9 |
| Admixture (oz/yd³) | 3 |
| Slump before addition | 4.2 |
| Revs before addition | 40 |
| Load size (yd) | 9.0 |
| Reason | Slump below target |

8:01 AM

| | |
|---|---|
| Water (gal/yd³) | 0.5 |
| Admixture (oz/yd³) | 0 |
| Slump before addition | 4.9 |
| Revs before addition | 190 |
| Load size (yd) | 9.0 |
| Reason | Sneak water |

FIG. 3

SNEAK WATER DETECTION FOR CONCRETE DELIVERY VEHICLES

FIELD OF THE INVENTION

The present invention relates to manufacturing of concrete, and more particularly to a system and method for detecting and evidencing previously undocumented fluid additions into the concrete mixer drum of a delivery vehicle.

BACKGROUND OF THE INVENTION

Concrete is made using a cementitious binder, aggregates (e.g., sand and coarse stone), water, and optionally one or more chemical admixtures for modifying slump (a rheological property), strength, and/or other properties. The slump of the concrete can be increased by adding water. However, too much water can lead to decreased compressive strength in the resultant concrete when hardened.

It is known that the "slump" of concrete in ready-mix delivery trucks can be controlled by using sensors to monitor the energy required for rotating the mixing drum, such as by monitoring the torque applied to the drum by measuring hydraulic pressure and adjusting fluidity by adding fluid into the mixing drum. Examples of fluid dispensing systems are disclosed in U.S. Pat. Nos. 4,008,093 and 5,713,663.

Various automated slump monitoring systems having fluid dispensing capability are described for background purposes as follows. The term "automated slump monitoring" will be used herein to include systems that measure the concrete on a continuous basis and modify the slump of the concrete through dispensing of water, chemical admixture, or both.

In U.S. Pat. No. 4,356,723 (1982), Fay taught that the hydraulic pressure required for rotating the mix drum, when measured at constant rotation speed, provided an indication of slump state, and taught that this could be measured at the building site when the concrete was to be discharged. The operator could add water from a tank on the truck during loading, transit, or delivery using a valve, and the slump could be adjusted at delivery. See e.g., U.S. '723 at column 4, lines 3 et seq.

In U.S. Pat. No. 4,318,177, Rapp et al. disclosed that water addition to concrete can be controlled through empirical testing of consistency by initially feeding a quantity of water to the batch reduced by an amount equivalent to the moisture content of the aggregates of the batch at maximum intrinsic moisture content, and thereafter incrementally adding measured amounts of water while measuring consistency after each water addition, and storing these values for the respective recipe and batch size.

In U.S. Pat. No. 4,544,275, Hudelmaier taught a system for automatically closing the water supply valve on the mixing truck when the drive torque applied to the mixing drum exceeded an adjustable limit. For special conditions, such as a change in climate, the system could also provide for opening of a water supply valve for admitting a limited, preselected amount of water. See e.g., Abstract of '275 patent.

In U.S. Pat. No. 5,713,663, Zandberg et al. disclosed a mixing truck wherein the hydraulic drive for rotating the mixing drum was monitored and liquid component was added into the concrete to approach a predetermined minimum torque loading on the hydraulic drive. A water volume sensor was provided to measure the amount of water added to the concrete. The prevention of excess liquid additions could also be controlled using this apparatus.

In U.S. Pat. No. 5,752,768, Assh disclosed a system for calculating slump of concrete in a mixer and for calculating the amount of water required to change from the current slump to a target slump for the purpose of deciding how much water to add into the concrete to increase the slump.

In U.S. Pat. No. 6,484,079), Buckelew emphasized the need for automated monitoring and reporting of the slump of the concrete to a remote location, such as the dispatch center, due to driver mistakes or other occasions in which water was intentionally added to the concrete and not reported. For example, Buckelew noted that sometimes the foreman at the delivery site would often request that water be incorporated into the concrete to ease installation; drivers could be persuaded to add water before pouring and to avoid reporting the water addition (See column 2, lines 11-24). Buckelew attempted to resolve this problem by providing a status sensor and measuring the current slump and comparing this to a delivery slump, as well as a water counter for determining the amount of water added to the concrete. Data regarding this delivery status could be transmitted to the dispatch center. Buckelew did not provide a means for determining whether the slump information indicated a change in fluid content or other variations in the concrete.

In U.S. Pat. No. 8,082,431 (which is owned by the common assignee hereof), Cooley et al. disclosed a delivery vehicle system having a hydraulic sensor coupled to the hydraulic drive and configured to sense hydraulic pressure required to turn the mixing drum and a rotational sensor configured to sense the rotational speed of the mixing drum. The system contained flow valves and flow meters for measuring and controlling water or chemical admixture addition into the concrete.

In U.S. Pat. No. 8,118,473 (which is owned by the common assignee hereof), Compton et al. disclosed a delivery vehicle system wherein a sensing of the rotational speed of the concrete mixing drum is used to qualify a calculation of current slump based on the hydraulic pressure required to turn the mixing drum. This system also contained flow valves and meters which could be controlled by computer to measure and control the amount of water added to the mixing drum to reach a desired slump, and may also obtain data on water manually added to the mixing drum by a hose connected to the truck water supply via a separate flow sensor or from a status system (See column 5, lines 9-22).

In Ser. No. 12/993,844, Berman disclosed a concrete mixing control apparatus with a sensor mounted on the interior surface of a concrete mixer drum and configured to monitor stress or pressure, which could be related to concrete slump. The system further comprised a liquid flow meter. Berman further disclosed a method of determining the amount of water needed to adjust the current slump to the target slump and then adding this amount of water.

In U.S. Ser. No. 13/500,643, Beaupre et al. disclosed a rheological probe for mounting inside a rotating mixing drum and configured to sense drum speed and force, and using collected data from the probe to determine slump and other rheological properties of the concrete.

SUMMARY OF THE INVENTION

The present inventors have discovered that despite the use of automated slump control systems on concrete mix delivery vehicles, including ones having onboard water tanks connected to an onboard flow meters and onboard valve that are in turn connected to onboard computer processing units (CPUs), truck drivers still too frequently introduce water from undocumented sources into the concrete mix contained in the concrete mixing drum, much to the potential detriment of the concrete product which could thereby suffer a reduction in compressive strength not accounted for or foreseen by the ready mix producer and its customers.

The present inventors realize that concrete truck drivers may introduce water into the mix from a water hose at the ready mix plant. This is done for a number of reasons known to the driver, such as to augment slump and to ease the power load on the hydraulic drive which rotates the mixing drum, to avoid taxing onboard water and/or chemical admixture reserves, to expedite pouring, placement, and finishing of the concrete at the delivery site, or indeed for all these reasons. Undocumented water can be added from any number of sources, such as from water hoses at fuel stations, rest stops, restaurants, and delivery sites.

Surreptitious additions of water are most likely to occur at delivery to make the concrete pour faster and to enable a crew to "finish" the surface faster. In any event, this circumvents the onboard valves, flow meters, or other equipment sensors that signal to the CPU the fact and extent of fluid additions into the concrete.

The above described undocumented fluid additions are referred to by the present inventors as "sneak" fluid additions, which are usually done by adding water rather than the more expensive chemical admixtures. The term "sneak fluid" as used herein, will include any fluid introduced into concrete for purposes of increasing its slump, but not added through a measuring device, such as a pump or flow meter, configured for determining the amount of water added to the mixing drum. Sneak fluid additions thus may include "sneak water" and/or "sneak admixture" additions. The inventors use the concept of "slump" for convenience, but it will be understood that this stands for related rheological properties such as slump flow, yield stress, DIN flow, etc. which are similarly affected by sneak fluid additions. Similarly, while automated slump monitoring systems are known for controlling slump which involve correlating the slump of concrete as measured by standard slump cone with the force (e.g., hydraulic) used for rotating he mixing drum, the term "automated slump monitoring system" as used herein can include other devices for monitoring concrete rheology. For example, it is possible to monitor on a continuous basis changes in force exerted on a probe placed within the concrete mixing drum.

Sneak water additions can severely disrupt the expectation of the ready-mix producer and customers that the delivered concrete will achieve certain strength targets. While commercially available automated slump monitoring systems provide the ability to monitor water additions from onboard tank using flow meters, valves, or other devices which are connected to the CPU, the ability to detect sneaked fluids has not really existed because drivers can circumvent automated systems to deliver concrete that has been weakened by undocumented additions.

Due to critical relationship between water-to-cement ratio and compressive strength, concrete specifications typically set a maximum water-to-cement ratio and require that an inspector at the jobsite confirm that no more than a maximum amount of water has been added to the concrete. The inspector checks the batch ticket, which shows the amount of water and cement added at the batch plant, as well as data from any flow meters on the truck. If the sum of water added from all documented sources causes the maximum water-to-cement ratio to be exceeded, the inspector will reject the load of concrete. This results in significant cost for the concrete producer in terms of lost time and materials. The pay or work hours for a given driver can be reduced if too many loads are rejected. Therefore, if drivers want to increase slump to meet a slump requirement, they are tempted to add water in a manner that will not be documented by on-board valves or flow meters.

A further challenge in accurately recording all additions of water has been that concrete trucks typically have a hose for washing down the outside of the truck and the delivery chute. If a flow meter is installed on this hose, it will not be possible to distinguish whether the driver used this hose to wash down the outside of the truck or chute, or whether the driver used the hose to add water into the drum.

The present invention is directed to a novel method and system for determining the amount of water added into the concrete in the mixing drum of a concrete delivery vehicle, particularly including sneak fluid additions. Preferred systems and methods of the invention permit the amount of sneak fluid to be quantified and recorded. The CPU of the automated slump monitoring system is programmed to detect when a given slump increase exceeds a predetermined minimum slump increase, to confirm that this fluid was not added by or through operation of the automated slump monitoring system (where the CPU does not detect that a flow meter, sensor, valve or other onboard device was not activated to administer water or admixture into the concrete), and calculate the amount of sneak fluid added into the concrete mixing drum.

Preferred systems and methods of the invention provide for the capability of determining the total amounts of sneak fluid added, and, by considering the amount of fluid added by the automated slump monitoring system, can calculate the total amount of fluids (water and chemical admixture, whether authorized or monitored by the system or not) incorporated into the concrete mixing drum.

Figure 2:
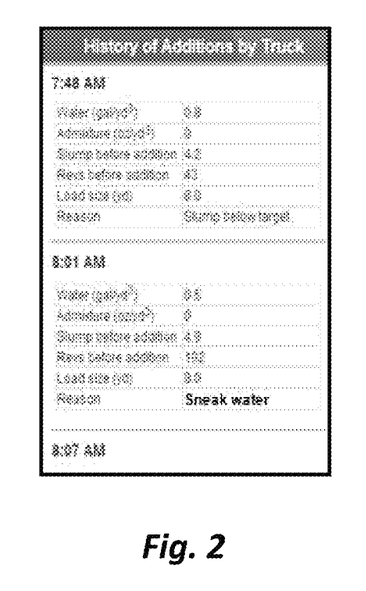
FIG. 2 depicts an exemplary method (as well as operation of an exemplary system) of the present invention wherein sneak water is reported on the electronic screen of a hand-held device such as might be used by jobsite inspector or contractor.

These values can then be displayed on computer or phone screen or paper (see e.g., FIG. 2). The automated slump monitoring system can be programmed, as another example, to trigger an alarm (e.g., at the dispatch station, customer laptop), and, as still further example, to record the data in a CPU-accessible location on the truck or at the dispatch center. Preferably, these capabilities are incorporated into the CPU-controlled automated slump control system.

An exemplary process of the invention for detecting fluid addition into concrete contained within a delivery vehicle mixing drum comprises: (A) monitoring changes in a rheology property of a concrete mix contained within a delivery vehicle mixing drum on a continuous basis by means of a computer processor unit (hereinafter "CPU"); (B) detecting when a change in monitored rheology property of the concrete mix exceeds a predetermined minimum rheology change value which has been inputted into or made accessible to said CPU; (C) determining, for each detected rheology change beyond said predetermined minimum rheology change value, whether such rheology change beyond said predetermined minimum rheology change value is due to fluid addition not monitored by said CPU and is sustained beyond a predetermined minimum period of time and/or predetermined minimum number of drum rotations, or both (hereinafter "sneak fluid" condition); and (D) reporting the occurrence of a sneak fluid condition as determined in (C) or otherwise preventing or restricting further fluid additions by at least one of the following modalities: (i) initiating an audible alarm, a visual alarm, or both; (ii) providing an indication of the amount of the sneak fluid added into the mixing drum; (iii) providing an indication of total fluid amounts including said sneak fluid added in the mixing drum; and/or (iv) preventing or limiting further fluid additions using valve, flow meter, or fluid tanks on said delivery vehicle into the mixing drum.

As previously mentioned, an exemplary rheology property is slump, and automated slump monitoring systems in current use would be able to measure the rheology change as an increase in slump, when water or plasticizing admixture is added into the mixing drum, and thus the slump increase and predetermined minimum slump change value would be reflected as a positive number. This would be similar for the case of slump flow and DIN flow; but yield stress would be reflected in terms of a negative value as it reflects resistance to flow rather than susceptibility to flow.

In further exemplary methods and systems of the present invention, step (C) further comprises determining whether such sustained rheology change is due to a false alarm condition, such as tilting of the mixing drum (which could skew rheology monitoring temporarily) or such as where the automated slump monitoring system detected a leakage condition on the delivery vehicle (such as defective valve).

Further advantages and features of the invention are described in further detail hereinafter.

BRIEF DESCRIPTION OF THE DRAWINGS

Further advantages and features of the present invention may be more readily comprehended when the following detailed description of preferred embodiments is taken in conjunction with the appended drawings wherein.

DETAILED DESCRIPTION OF EXEMPLARY EMBODIMENTS

The term "concrete" as used herein will be understood to refer to materials including a cement binder (e.g., Portland cement optionally with supplemental cementitious materials such as fly ash, granulated blast furnace slag, limestone, or other pozzolanic materials), water, and aggregates (e.g., sand, crushed gravel or stones, and mixtures thereof), which form a hardened building or civil engineering structure when cured. The concrete may optionally contain one or more chemical admixtures, which can include water-reducing agents (so called because they permit a cut in the water required water while maintaining plasticity), mid-range water reducing agents, high range water-reducing agents (often called "superplasticizers"), viscosity modifying agents, corrosion-inhibitors, shrinkage reducing admixtures, set accelerators, set retarders, air entrainers, air detrainers, strength enhancers, pigments, colorants, fibers for plastic shrinkage control or structural reinforcement, and the like.

As mentioned previously in the background references (which are incorporated fully herein by reference), the concrete industry has begun to deploy delivery vehicles (mixing trucks) having automated slump monitoring systems. The term "automated slump monitoring systems" or "slump monitoring" as used herein means and includes at least one computer processing unit (CPU) that is electrically or wirelessly connected to sensors, such as hydraulic and/or electric sensors for measuring the energy for rotating the mixing drum, speed sensors for measuring the speed of drum rotation, temperature sensors for monitoring the atmospheric temperature as well as the mix temperature, valves, flow meters, and other devices. The CPU is also electrically or wirelessly connected to various equipment onboard the vehicle such as actuators for operating valves, flow meters, dispensing pumps (for fluids such as water, chemical admixtures), and the like.

Exemplary concrete mixing drums contemplated for use in the present invention include those which are customarily mounted for rotation on ready-mix delivery trucks or on stationary mixers which may be found in mixing plants. Such mixing drums have an inner circumferential wall surface upon which at least one mixing blade is attached to the inner surface so that it rotates along with the mixing drum and serves to mix the concrete mix, including the aggregates contained within the mix. It is believed that a number of exemplary embodiments of the invention may be practiced using commercially available automated concrete mix monitoring equipment with slight modifications as would be apparent in view of the invention disclosed herein. Such concrete mix monitoring equipment is commercially available under the trade name VERIFI® from Verifi LLC, West Chester, Ohio, and Cambridge Mass.

Concrete trucks are commonly equipped with water tanks connected by a hose line directed into the drum opening. In this manner, water can be dispensed into the drum under air pressure in the tank or by pump. Such tank dispensing devices are disclosed in U.S. Pat. No. 4,544,275, U.S. Pat. No. 7,842,096 and U.S. patent application Ser. No. 11/955, 737, for example. When such admixture tanks are present, the tank is typically connected to the same hose line used to discharge water into the drum. The chemical admixture may be dispensed into the water line under air pressure or by tank to the pump. This is exemplified in U.S. Pat. No. 7,730,903. Alternatively, chemical admixtures and water may be dispensed using different lines into the mixing drum.

Exemplary systems and methods thus comprise the use of a computer processing unit (CPU) in combination with a hydraulic sensor for measuring the hydraulic pressure required to rotate the concrete mixer drum, a speed sensor for measuring the speed of mixer drum rotation, and preferably both of these sensors, with the system automatically adjusting a rheology property of the concrete (e.g., slump, slump flow, yield stress or resistance to flow, thixotropy, or other rheology property), by introducing a liquid chemical admixture and/or water through the system. As mentioned in the summary section, while the present invention focuses on "slump" as the rheological property which is being monitored and adjusted, it will be evident to one of ordinary skill in view of the disclosure herein that the term "slump" can be used interchangeably with other rheological properties, such as slump flow, yield stress, DIN flow, and other rheological characteristics.

The exemplary delivery vehicle systems taught by Cooley et al. in U.S. Pat. No. 8,082,431 and by Compton et al. in U.S. Pat. No. 8,118,473 (both owned by the common assignee hereof) contained CPU-controlled systems for automated slump monitoring and control, wherein hydraulic pressure required to turn the drum and rotational speed of the mixing drum are monitored, and flow valves and meters are controlled by the CPU to control water added to the mixing drum to reach the desired slump. Compton et al. mentioned that water manually added into the drum from a hose connected to an onboard water tank could also be monitored via separate flow sensor (meter). Such systems as disclosed by Cooley et al. and Compton et al. can be modified according to the present invention to further provide monitoring over previously undocumented "sneak water" additions.

The present inventors believe that various other of the slump monitoring systems and modifications owned by the common assignee hereof can be advantageously employed in conjunction with the sneak water detection method and system of the present invention, including the systems in aforementioned U.S. Pat. Nos. 8,020,431, and 8,118,473; the thixotropy monitoring system disclosed in U.S. Ser. No. 12/933,947 (Publ. No. 2011/0029134 A1); the slump monitoring system employing Fast Fourier Transform process disclosed in U.S. Ser. No. 13/260,391 (Publ. No. 2012/0020180 A1); the horizontal slump flow monitoring system disclosed in U.S. Ser. No. 13/258,104 (Publ. No. 2012/0016523 A1); the slump monitoring system based on nominal dosage profiles as disclosed in U.S. Ser. No. 12/821,451 (Publ. No. 2011/0320040 A1); and the slump monitoring system employing fluid dispensing as disclosed U.S. Ser. No. 13/076,687 (not yet published as of this filing date), which are all incorporated herein by reference.

It is known that algorithms or relations between the measured amount of water and/or chemical admixture and its corresponding effect on increasing the slump of a given concrete can be ascertained and established using commercial automated slump monitoring systems. An automated slump monitoring and control system which performs these functions is commercially available from Verifi LLC, West Chester, Ohio (and Cambridge, Mass.), under the VERIFI® name.

Figure 1:
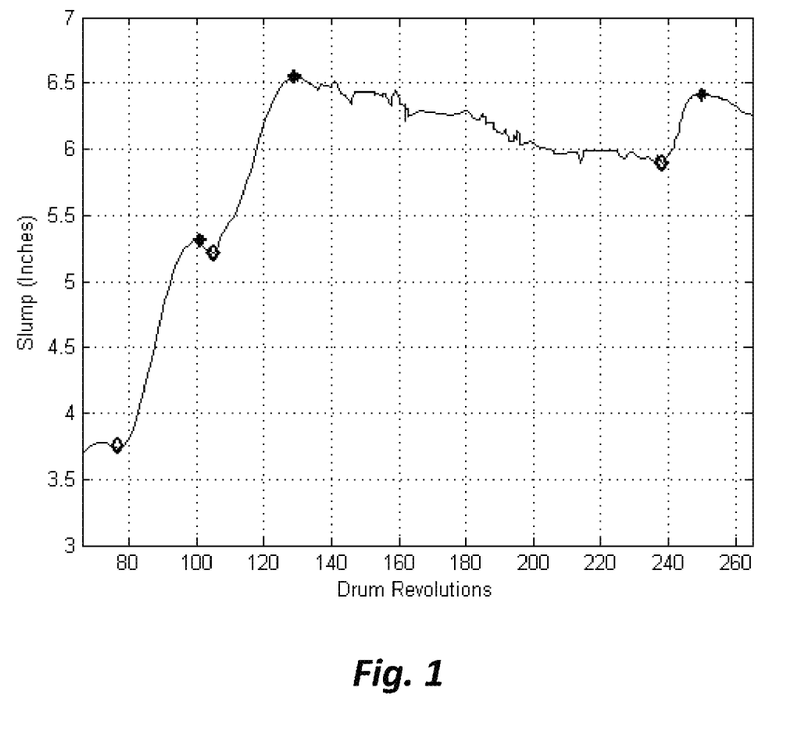
FIG. 1 is a graphic illustration of an exemplary method (as well as operation of an exemplary system) of the present invention wherein documented fluid additions are made through a monitored valve into concrete contained in a mixing drum, and also in the form of a "sneak" fluid (e.g., water) addition, and the resultant concrete slump (along vertical axis, in terms of inches) is monitored during a segment of the mixing process which is measured in terms of mixing drum rotations (along horizontal axis)

As illustrated in FIG. 1, the slump of a concrete mix contained in a mixing drum on a delivery vehicle (e.g., truck) containing an automated slump monitoring system (e.g., VERIFI® control system) monitors the slump of the concrete in the mixing drum on a continuous basis. By "continuous," it is intended to mean that the system can measure slump at periodic intervals over time or over a certain number of drum rotations. For example, at the $78^{th}$ drum rotation, water (in the amount of about 1.5 gallons per cubic yard of concrete) is shown added by the driver from an onboard water tank through an onboard valve and meter that are connected to computer processing unit (CPU), and the valve is then closed at the $91^{st}$ mixing drum rotation. The ensuing slump of the concrete continues to increase well after the closing of the valve. By the $100^{th}$ drum rotation, the slump will have increased by approximately 1.5 inches (from about 3.75 to 5.25 inches). The valve opening at the $78^{th}$ drum rotation and the valve closing at the $91^{st}$ drum rotation are monitored by the onboard CPU, such that the automated slump control system records the increase of slump and can attribute the amount of water measured by a flow meter connected in the same water line that was controlled by the valve (which the opening and closing of which are controlled and monitored by the CPU).

FIG. 1 also illustrates how the methods and systems of the present invention provide for monitoring, and possible documentation (or alarm, evidence, or other indicia) of water being "sneaked" into the concrete mix by a driver who attempts to circumvent the automated slump control system on board the truck by adding water from a water source that was not monitored through onboard valves or flow meters (or other sensors). For example, the driver might employ a water hose that is not connected to a valve or flow meter or other sensor connected to the onboard CPU. This is shown in FIG. 1 between approximately 105-130 drum rotations in which the driver has added one gallon of water per cubic yard of concrete into the mixing drum. The automated slump monitoring system will not have recorded any signal from the water flow valve or meter, while at the same time recording the increase of slump between 105 drum rotations (where slump is approximately 5.25 inches) and 130 drum rotations (where slump is approximately 6.5 inches).

An exemplary process of the invention is contemplated for detecting fluid addition, including "sneak fluid" addition, into concrete mixes in a delivery vehicle mixing drum. This comprises: (A) monitoring changes in a rheology property of a concrete mix (which may be selected from slump, slump flow, DIN flow, and yield stress) contained within a delivery vehicle mixing drum on a continuous basis by means of a computer processor unit (CPU"); (B) detecting when a change in monitored rheology property of the concrete mix exceeds a predetermined minimum rheology change value which has been inputted into or made accessible to said CPU; (C) determining, for each detected rheology change beyond said predetermined minimum rheology change value, whether the rheology change beyond the predetermined minimum rheology change value is due to fluid addition not monitored by said CPU (or, in other words, the fluid is not monitored by valve, flow meter, pump, or other equipment sensors connected to the system CPU) and is sustained beyond a predetermined minimum period of time, a predetermined minimum number of drum rotations, or beyond both (hereinafter "sneak fluid" condition); and (D) reporting the occurrence of a sneak fluid condition as determined in (C) or otherwise preventing or restricting further fluid additions into the mixing drum, by employing at least one of the following modalities: (i) initiating an audible alarm, a visual alarm, or both; (ii) providing an indication of the amount of the sneak fluid added into the mixing drum; (iii) providing an indication of total fluid amounts including said sneak fluid added in the mixing drum; and/or (iv) preventing or limiting further fluid additions using valve, flow meter, or fluid tanks on said delivery vehicle into the mixing drum.

Due to availability of slump monitoring systems which can be modified to accomplish the present invention as will be evident to those of ordinary skill in view of the disclosures herein, an exemplary rheology property is slump. Automated slump monitoring systems, such as VERIFI® slump monitoring systems can be modified to measure rheology change as an increase in slump, when water or plasticizing admixture is added into the mixing drum, and thus slump increase and predetermined minimum slump change value would be reflected as positive numbers. In the following description, slump will be used as an exemplary rheology property for convenience of explication.

In step (A) of the above-described method, the monitoring of the slump of a concrete mix contained within the delivery truck mixing drum on a continuous basis can be accomplished by computer processor unit (CPU) and storing the monitored slump history values in a CPU-accessible location (memory storage device). The CPU and storage devices can be located on the truck or at a remote location and accessed wirelessly. The slump of concrete in the mixing drum can be monitored and controlled by CPU and slump profiles stored in CPU-accessible memory, for example as taught in U.S. Pat. Nos. 8,020,431, and 8,118,473.

Tanks containing additive fluids (e.g., water and/or chemical admixtures), flow meter(s) or other sensors for measuring the volume of fluid dispensed from the tank, and a valve for opening and closing the line for feeding fluid into the mixing drum, are mounted on the delivery vehicle and can be connected electrically and/or electronically to a CPU on the truck or at the dispatch center. Other fluid dispensing and flow monitoring equipment, such as pressurized air source for expelling fluids from fluid-containing tanks through valves into the concrete mixing drum may alternatively be deployed.

Preferred systems and methods of the invention involve the use of a sensor for monitoring the hydraulic energy or power required to rotate the mixing drum as well as a sensor for measuring the rotational speed of the mixing drum and the number of rotations. The advantages of using both a hydraulic sensor and rotational sensor were disclosed in the patents of Cooley et al. and Compton et al., and are realized in Verifi® control systems which are commercially available.

In step (B), which describes that the changes of the concrete slump (or other rheology property) are monitored continuously over the relevant time period and data is stored in a location accessible to the CPU, the data may be stored in memory devices located on the delivery truck and/or may be transmitted to the dispatch center or other remote location. This could also include, as another example, the laptop of the manager for the ready mix customer who is concerned that the concrete being delivered is not compromised by undocumented water additions.

In step (C), the exemplary method of the invention provides for the CPU to detect when the concrete slump increases over a predetermined minimum slump increase value, which is preferably 0.25 inch. The predetermined minimum slump value can be set at a higher level (e.g., 0.3 inch, 0.4 inch, etc.) as desired. The determination of whether a sneak fluid addition has occurred will involve the system CPU confirming that when the slump (or other rheology) change does reach or exceed the predetermined minimum change value, that this change is not due to fluid being administered into the concrete mixing drum using a valve, flow meter, pump, or other equipment on the delivery vehicle, and thus the system would determine that the fluid addition is attributable to another source other than from tanks on the truck. Commercially available slump monitoring systems, for example, have sensors on such equipment to permit the CPU to determine whether fluid was added from the system.

In other exemplary methods and systems of the present invention, step (C) further comprises determining whether such sustained rheology change is due to a false alarm condition, such as tilting of the mixing drum (which could skew rheology monitoring temporarily) or where the automated slump monitoring system detected a leakage condition on the delivery vehicle (such as defective valve). The tilting of the mixing drum can be detected by using the appropriate sensor on the delivery vehicle, and connecting this sensor to the CPU so that a history of vehicle tilt angle can be recorded into CPU-accessible memory.

The CPU can be programmed to determine, for each measured slump increase which is detected to exceed the predetermined minimum slump value, whether the increase is maintained for a preselected period of time or beyond a preselected number of mixing drum rotations. Thus, if the CPU determines that concrete slump increases above the predetermined minimum slump value (e.g., 0.25 inch), then the CPU must determine whether this slump increase is maintained, preferably, for at least 5 mixing drum rotations, and more preferably for at least 10 mixing drum rotations. Alternatively, the CPU can determine whether a slump increase above the predetermined minimum slump value extends beyond a minimum 60 seconds; and, more preferably, beyond 45 seconds; and, most preferably, beyond 30 seconds.

The minimum drum rotations or time periods are believed by the present inventors to allow an automated slump monitoring system to filter out the effects of a false reading for slump increase, such as where the delivery vehicle hits an obstacle on the roadway which could temporarily jar the slump monitoring system. It is also envisioned that the CPU can be programmed to detect both conditions, i.e., both when the slump is detected to exceed the predetermined for the preselected period of time and beyond the preselected number of mixing drum rotations.

In exemplary embodiments, the CPU is programmed to calculate the amount of fluid added into the concrete mixing drum which was not monitored by or dispensed by operation of the CPU, or, in other words, not monitored by equipment on the truck (e.g., valve, flow meter, pump, tank, or other equipment on the delivery truck). In its continuous monitoring of the slump value of the concrete, the CPU is programmed to determine when slump stops increasing, so that total slump change due to the water addition can be determined. Thus, for the process illustrated in FIG. 1, the CPU determines that a slump increase begins at the $105^{th}$ drum rotation and ends at about the $130^{th}$ drum rotation; and thus the amount of water added to the concrete can be calculated by determining the total slump increase and calculating in accordance with pre-established corresponding relationships between water addition and slump change.

Other exemplary methods and systems of the invention provide that the CPU can trigger alarms, save (record) the data which evidences the "sneaked" fluid addition, and otherwise provide for various documentary or evidentiary means for providing alarm, record, graphic display, print out, ticket, or other manifestations of evidence that sneak fluid addition has occurred. Any of these manifestations can be used to confront the driver with evidence in an attempt to alter the behavior of surreptitious or inadvertent water additions which can harm the concrete. The CPU can also be programmed to restrict or limit further water additions made through onboard devices, including valve or valves for adding water and/or other fluids into the concrete.

Thus, for example, the CPU can trigger alarms could include alarms of an audible or visual nature. For example, the alarm could be mounted on the side of the truck, or could otherwise occur at the concrete dispatch center (mixing plant or other office). Preferably, the CPU calculates the total amount of sneak fluid (water) detected and added into the system, and more preferably indicates this amount along with the total amount of water, whether monitored by the automated slump control system or dispensed from undocumented sources, on computer or laptop screen, or otherwise printed out in the form of a paper document, "ticket," or even an electronic "ticket" that displays on a viewing screen or monitor display (e.g., laptop, handheld device such as palm size mobile phone or other device). The CPU can also be programmed to restrict or limit further amounts of water or other liquid from tanks onboard the concrete delivery vehicle.

The maximum water that can be added on the truck can be obtained from the batch software in the batching plant.

The batch software has the maximum water-to-cement ratio or maximum water content, as well as the actual amount of water that was added at the batching plant. The difference in these two values is the maximum amount of water that can be added after batching and before the completion of delivery.

Indeed, it is preferred that the CPU of the automated slump monitoring system be programmed to enact any number of these features, as might be preferred by the ready mix producer or its representative. In an exemplary system or method of the invention, the CPU could be programmed to generate a graphic, either on paper or monitor display, similar to FIG. 1 wherein the concrete slump level is displayed as a function of drum rotations (as shown in FIG. 1) or as a function of time or geographical location (where the system is equipped with global positioning capabilities) and each slump increase is demarcated such that the beginning of the slope designates whether an onboard valve, flow meter, or other flow sensor is open (confirming that the fluid addition was authorized or otherwise monitored by the system) or closed (confirming that the fluid addition was unauthorized or unmonitored and thus a "sneak" addition).

In further exemplary methods and systems of the invention, the CPU could be connected to the truck electrical system to activate the vehicle horn as the audible alarm and to activate the warning lights (blinking turn signals) as the visual alarm. This would be one way to curb the sneak water addition behavior of truck drivers or foremen at construction sites. For example, an architect or representative of the ready mix customer would readily be able to notice a concrete delivery mix truck on the site when its horns and lights were activated at once while it was attempting to make a delivery, and they would be able to generate a status report, ticket, or other record from the CPU to confirm that sneak water additions were made and to determine the total amount of water added into the concrete, in addition to the amount of sneak water that was added, and to make appropriate decisions as to whether the concrete needs to be returned to the dispatch center, used, or modified. Knowing the total amount of water added (documented as well as sneak fluid additions) will enable determinations by the automated slump monitoring system as to whether the concrete will be capable of reaching the desired strength profile.

In further exemplary methods and systems of the invention, where the CPU detects a slump increase beyond a pre-established minimum slump increase, and determines that the slump increase is maintained beyond the preselected period of time and/or beyond a preselected number of mixing drum rotations, the CPU is programmed to confirm that the fluid addition was not added by the CPU or by way of valve, flow meter, pump, or other equipment on board the concrete delivery vehicle (and this gives rise to the conclusion that a "sneak fluid" was added); and the CPU can also be programmed to determine whether the measured slump increase which exceeds the measured predetermined minimum increased amount is due to factors other than sneak fluid (water) additions, such as tilting of the mixing drum, and, if the measured slump increase is determined to be due to extraneous factors such as tilting of the mixing drum, the CPU is programmed to omit the slump increase data from the calculation of sneak fluid (water) addition.

Another factor causing an increase in slump without the addition of fluid is an increase in entrained air content. This can be addressed by providing a measurement of the air content, unit weight, or volume of concrete in the truck mixing drum (See e.g., U.S. Ser. No. 13/512,466 and PCT/US2010/028207) and determining whether an increase in slump can be attributed to an increase in concrete air content.

Still further exemplary methods and systems of the invention involve programming the CPU to determine whether fluid added is water or chemical agent or combination of both; and, if a combination, the CPU can be programmed to determine the respective amounts of water and chemical agent added. This can be done as the slump profile over drum rotations would be known, respectively, for water and for a given chemical admixture, and these slump profiles would be stored into CPU-accessible memory or storage locations. The slump-increasing behavior of superplasticizers would, for example, likely create a much smaller slope in the slump increase and take place in more drum revolutions compared to the slump-increasing behavior of water. Thus, if a driver attempted to sneak into the mixing drum using both superplasticizer and water additions, the CPU can be programmed to analyze the slump increase over drum rotations and to back-calculate the relevant amounts of sneak water and sneak plasticizer added based on the stored slump profile information in the CPU-accessible memory or storage locations. This computation of sneak fluid addition would be easier, for example, if the driver were to attempt to add sneak water at the same time that a superplasticizer or other rheology-enhancing additive was being dosed into the mixing drum by the automated slump control system. The CPU can be programmed to subtract the effect of the CPU-authorized fluid addition to calculate the amount of sneak water added.

The exemplary system and method could further distinguish between water and chemical admixture additions by measuring and analyzing the effect of the addition on rheology. For example, for a given change in slump, water has a greater effect on plastic viscosity than imparted by superplasticizer.

Exemplary systems of the invention for detecting sneak fluid additions therefore comprise: a hydraulic sensor monitoring the hydraulic device for rotating a concrete mix drum on a concrete delivery vehicle, a sensor for monitoring the rotation speed of the mix drum on a concrete delivery vehicle, flow meter or sensor and valve for monitoring addition of fluid into the mix drum of a concrete delivery vehicle, a computer processor unit (CPU) electrically or electronically connected to hydraulic sensor, rotational speed sensor, flow meter(s) or sensor(s) and valves (so as to measure the fact and extent or volume of fluids administered into the concrete mix drum) as well as to memory locations (whether onboard or remote) accessible to the CPU for storing and retrieving data and software programs effective for the CPU to instruct the system to perform steps A through D as previously described above and as claimed herein after.

An exemplary system of the invention for detecting fluid addition into concrete contained within a delivery vehicle mixing drum comprises: an automated rheology monitoring system effective for monitoring changes in a rheology property of a concrete mix contained within a delivery vehicle mixing drum on a continuous basis by means of a computer processor unit (hereinafter "CPU") (said rheology property being selected from slump, slump flow, DIN flow, and yield stress); said CPU being programmed to detect when a monitored rheological property of a concrete mix change exists due to an addition of fluid into the delivery vehicle mixing drum, beyond a predetermined minimum rheology change value; said CPU being further programmed to determine for each detected rheology change beyond said predetermined minimum rheology change value whether such rheology change beyond said predetermined minimum rheology change value is sustained beyond a predetermined minimum period of time and/or predetermined minimum number of drum rotations, or both (hereinafter "sneak fluid" condition); and said CPU being programmed to report the occurrence of a sneak fluid condition, using at least one of the following modalities: (i) initiating an audible alarm, a visual alarm or display, or both; (ii) providing an indication of the amount of the sneak water added into the mixing drum; (iii) providing an indication of total fluid amounts including said sneak fluid added in the mixing drum; and/or (iv) preventing or limiting further fluid additions using valve, flow meter, or fluid tanks on said delivery vehicle into the mixing drum.

Preferred systems of the invention are automated slump monitoring devices are those which provide a visual alarm or display of detected sneak water addition, such as exemplary in FIG. 2 by the depicted screen of a hand held device.

Figure 3:
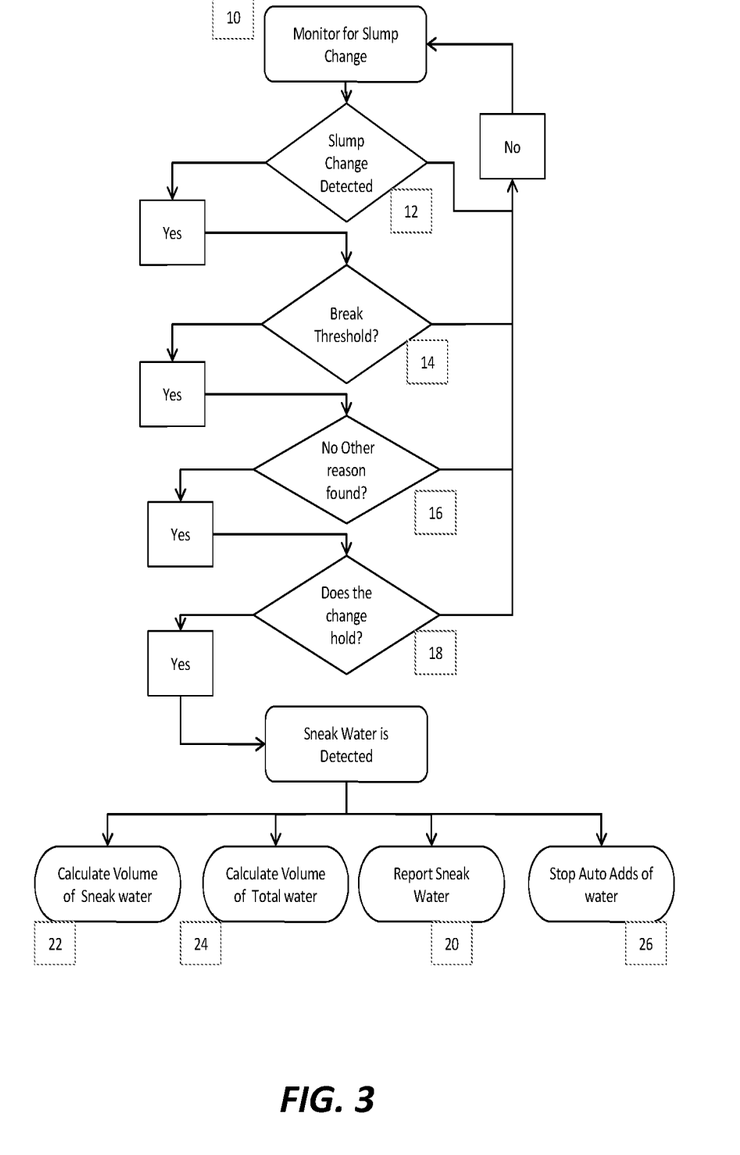
FIG. 3 illustrates using block diagram the method of the present invention for detecting fluid addition in concrete contained within a delivery vehicle mixing drum.

FIG. 3 illustrates using block diagram the method of the present invention for detecting fluid addition in concrete contained within a delivery vehicle mixing drum, comprising: (A) monitoring changes in a rheology property of a concrete mix contained within a delivery vehicle mixing drum on a continuous basis by means of a computer processor unit (designated at 10); (B) detecting when a change in monitored rheology property of the concrete mix exceeds a predetermined minimum rheology change value which has been inputted into or made accessible to the computer processor unit (designated at 12); (C) determining, for each detected rheology change beyond the predetermined minimum rheology change value (designated at 14), whether such rheology change beyond the predetermined minimum rheology change value is due to fluid addition not added using pump, valve, flow meter, sensor or other onboard device monitored by the computer processor unit (hereinafter "sneak fluid") and is sustained beyond a predetermined minimum period of time, a predetermined minimum number of drum rotations, or both (hereinafter "sneak fluid condition") (designated at 18); and (D) reporting the occurrence of a sneak fluid condition as determined in (C) or otherwise preventing or restricting further fluid additions by at least one of the following modalities: (i) initiating an audible alarm, a visual alarm, or both (designated at 20); (ii) providing an indication of the amount of the sneak fluid added into the mixing drum (designated at 22); (iii) providing an indication of total fluid amounts including said sneak fluid added in the mixing drum (designated at 24); and/or (iv) preventing or limiting further fluid additions using valve, flow meter, or fluid tanks on said delivery vehicle into the mixing drum (designated at 26).

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

The invention claimed is:

1. A process for detecting fluid addition into concrete contained within a delivery vehicle mixing drum, comprising:
    (A) monitoring changes in a rheology property of a concrete mix contained within a delivery vehicle mixing drum on a continuous basis by means of a computer processor unit (hereinafter "CPU");
    (B) detecting when a change in monitored rheology property of said concrete mix exceeds a predetermined minimum rheology change value which has been inputted into or made accessible to said CPU;
    (C) determining, for each detected rheology change beyond said predetermined minimum rheology change value, whether such rheology change beyond said predetermined minimum rheology change value is due to fluid addition not added using pump, valve, or flow meter monitored by said CPU (hereinafter "sneak fluid") and is sustained beyond a predetermined minimum period of time, a predetermined minimum number of drum rotations, or both (hereinafter "sneak fluid condition"); and
    (D) reporting the occurrence of a sneak fluid condition as determined in (C) or otherwise preventing or restricting further fluid additions by at least one of the following modalities: (i) initiating an audible alarm, a visual alarm, or both; (ii) providing an indication of the amount of the sneak fluid added into the mixing drum; (iii) providing an indication of total fluid amounts including said sneak fluid added into the mixing drum; and/or (iv) preventing or limiting further fluid additions using valve, flow meter, or fluid tanks on said delivery vehicle into the mixing drum.

2. The process of claim 1 wherein said rheology property is selected from slump, slump flow, and DIN flow.

3. The process of claim 2 wherein said predetermined minimum rheology change value is a positive number.

4. The process of claim 3 wherein said predetermined minimum rheology change value is 0.15-1.0 inch increase in slump.

5. The process of claim 3 wherein said predetermined minimum rheology change value is at least 0.25 inch increase in slump.

6. The process of claim 1 wherein, after a rheology change exceeding said predetermined minimum rheology change value has been sustained beyond a predetermined minimum period of time or predetermined minimum number of drum rotations, step (C) further comprises determining whether such sustained rheology change is due to a false alarm condition.

7. The method of claim 6 wherein said false alarm condition is caused by tilting of the mixing drum.

8. The method of claim 6 wherein said false alarm condition is caused by leakage of fluid from fluid dispensing equipment on the concrete delivery vehicle.

9. The process of claim 1 wherein said predetermined minimum period of time, as described in step (C), is at least 30 seconds in duration.

10. The process of claim 1 wherein said predetermined minimum period of time, as described in step (C), is at least 45 seconds in duration.

11. The process of claim 1 wherein said predetermined minimum period of time, as described in step (C), is at least 60 seconds in duration.

12. The process of claim 1 wherein said preselected minimum number of drum rotations is 5.

13. The process of claim 1 wherein preselected minimum number of drum rotations is 10.

14. The process of claim 1 wherein said rheology property monitored is slump flow.

15. The process of claim 1 wherein said rheology change is monitored using at least one sensor for measuring hydraulic pressure used for rotating said mixing drum.

16. The process of claim 1 wherein said rheology change is monitored using a sensor placed into the mixing drum.

17. A concrete rheology monitoring system effective for performing the process of claim 1.

18. A system for detecting fluid addition into concrete contained within a delivery vehicle mixing drum, comprising: an automated rheology monitoring system effective for monitoring changes in a rheology property of a concrete mix contained within a delivery vehicle mixing drum on a continuous basis by means of a computer processor unit (hereinafter "CPU"); said CPU being programmed to detect when a monitored rheological property of a concrete mix change exists due to fluid addition not added by pump, valve, or flow meter monitored by said CPU (hereinafter "sneak fluid") and is beyond a predetermined minimum rheology change value; said CPU being further programmed to determine for each detected rheology change beyond said predetermined minimum rheology change value whether such rheology change beyond said predetermined minimum rheology change value is sustained beyond a predetermined minimum period of time, a predetermined minimum of drum rotations, or both (hereinafter "sneak fluid condition"); and said CPU being programmed to report the occurrence of a sneak fluid condition, using at least one of the following modalities: (i) initiating an audible alarm, a visual alarm or display, or both; (ii) providing an indication of the amount of the sneak fluid added into the mixing drum; (iii) providing an indication of total fluid amounts including said sneak fluid added in the mixing drum; and/or (iv) preventing or limiting further fluid additions using valve, flow meter, or fluid tanks on said delivery vehicle into the mixing drum.

19. The system of claim 18 wherein said automated rheology monitoring system is effective to monitor slump changes and to provide a visual alarm or display of detected sneak fluid addition.

* * * * *